United States Patent
Sun et al.

(10) Patent No.: US 12,044,610 B1
(45) Date of Patent: Jul. 23, 2024

(54) GROUNDWATER LEVEL ELEVATION MEASUREMENT METHOD, GROUNDWATER STORAGE MEASUREMENT SYSTEM, AND APPLICATION

(71) Applicant: Zhejiang University, Zhejiang (CN)

(72) Inventors: Hongyue Sun, Zhejiang (CN); Xu Wang, Zhejiang (CN)

(73) Assignee: Zhejiang University, Zhoushan (CN)

( * ) Notice: Subject to any disclaimer, the term of this patent is extended or adjusted under 35 U.S.C. 154(b) by 0 days.

(21) Appl. No.: 18/600,825

(22) Filed: Mar. 11, 2024

(30) Foreign Application Priority Data

Nov. 10, 2023 (CN) .......................... 202311498762.4

(51) Int. Cl.
*G01N 33/18* (2006.01)
*G01N 15/08* (2006.01)

(52) U.S. Cl.
CPC ......... *G01N 15/0826* (2013.01); *G01N 33/18* (2013.01)

(58) Field of Classification Search
CPC ........................... G01N 15/0826; G01N 33/18
See application file for complete search history.

(56) References Cited

U.S. PATENT DOCUMENTS

| | | | |
|---|---|---|---|
| 2012/0041692 A1* | 2/2012 | Suk ........................... | E03B 3/06 702/45 |
| 2014/0195174 A1* | 7/2014 | Machuga ........... | G01N 33/1886 702/55 |
| 2017/0044894 A1* | 2/2017 | Surowinski .............. | G01C 5/06 |
| 2018/0188089 A1* | 7/2018 | McKenna ................ | E21B 47/04 |
| 2021/0263062 A1* | 8/2021 | Xu ............................ | G01P 5/18 |
| 2024/0053508 A1* | 2/2024 | Ram ....................... | G01W 1/10 |

FOREIGN PATENT DOCUMENTS

| | | |
|---|---|---|
| CN | 100359297 C | 1/2008 |
| CN | 104330132 B | 5/2017 |
| CN | 104316144 B | 6/2017 |
| CN | 105424139 B | 8/2018 |
| JP | 2021148757 A | 9/2021 |

OTHER PUBLICATIONS

Notice of Allowance of counterpart Japanese Patent Application No. 2023-198602 issued on Feb. 27, 2024.

* cited by examiner

*Primary Examiner* — Eric S. McCall

(57) ABSTRACT

A groundwater level elevation measurement method is provided. A permeable cylinder is drilled at a measurement site to ensure that groundwater enters the permeable cylinder. A water inlet of an aqueduct extends below the liquid level in the cylinder, and a drainage outlet thereof is led to the ground. A stable drainage flow rate is detected, and a water level elevation at the water inlet is calculated according to the formula. An optimization method is to detect the flow rate after a stable negative pressure is introduced, and then calculate the water level elevation at the water inlet. According to the groundwater storage monitoring and measurement system of the present invention, a matrix of water level monitoring sites is laid out, groundwater level elevations at all sites and related data are measured and collected, and water storage characteristic data of a groundwater measurement space is constructed.

10 Claims, 4 Drawing Sheets

GROUNDWATER LEVEL ELEVATION MEASUREMENT METHOD, GROUNDWATER STORAGE MEASUREMENT SYSTEM, AND APPLICATION

CROSS REFERENCE TO RELATED APPLICATIONS

The present application claims the benefit of Chinese Patent Application No. 202311498762.4 filed on Nov. 10, 2023, the contents of which are incorporated herein by reference in their entirety.

TECHNICAL FIELD

The present invention relates to a geological environment monitoring and measurement technology, in particular to a device and system for monitoring groundwater-related physical variables, which belong to the technical field of groundwater environment monitoring and measurement.

BACKGROUND

Groundwater level is the most common and important groundwater monitoring element. At present, groundwater level monitoring is generally based on "burial depth" observation and measurement. There are two main types of instruments for automatically measuring groundwater levels: float type and pressure type. Float-type groundwater level meters can generally work in well logging pipes with a diameter of 5 cm to 10 cm. However, the sensitivity of small floats in sensing water level changes is poor, and the water level sensing sensitivity is easily affected by objective working conditions such as large groundwater burial depth and long suspension cables. Although the measurement accuracy of pressure-type water level meters is higher than the former, the quality of its measurement data depends on the quality of the monitoring water level environment. The measurement results are better under favorable conditions such as less sediment content and more stable water density. A device and method for measuring a groundwater level under negative pressure conditions (ZL2014105963763), a visual measurement method for a groundwater level under negative pressure conditions (ZL2014106122303), a groundwater level sealing measurement device based on an ultrasonic negative pressure, and its method (ZL2015107451162), a water level measurement device and method in a vacuum preloaded foundation reinforcement area (ZL2006100853372), etc., in the prior art have partially overcome the shortcomings of the above two types of measurement solutions by introducing negative pressure, vacuum and other technical features, but have not changed the basic features of their technical concepts that main working parts (measurement sensing components, etc.) of the measurement devices work inside the rock and soil mass, and technical improvements are always striving to capture and collect more subtle water level changes at the measurement sites. The basic features have led to obvious technical defects, including: firstly, the improvement of measurement technology can only be at the expense of equipment precision, which continuously drives up the cost of devices; secondly, in order to ensure the sensitivity of the measurement sensing components, the selection of monitoring sites needs more considerations to the terrain conditions of the rock mass, which may sacrifice important but difficult-to-construct monitoring points; thirdly, the controllability of external measurement operations is limited; and fourthly, it is difficult to maintain the main underground working parts, and once damaged and discarded, it will directly cause higher equipment, construction and other types of costs.

SUMMARY

The purpose of the present invention is to provide, in view of the shortcomings in the prior art, a groundwater monitoring and measurement technology in which main working parts of a measuring device are located above the ground.

In order to achieve the above object, the present invention first provides a groundwater level elevation measurement method, and its technical solution is as follows:

A groundwater level elevation measurement method, where a hole is drilled at a measurement site and a permeable cylinder is placed to ensure that groundwater enters the permeable cylinder, a water inlet of an aqueduct extends below the liquid level in the permeable cylinder, and a drainage outlet of the aqueduct is led to the ground; and after the drainage outlet discharges water steadily, a water level elevation $h_a$ at the water inlet is calculated according to an equation set of Equation 1, $$h_a = \min(h_{a1}, h_{a2}) \qquad \text{Equation 1-1}$$

$$\begin{cases} h_{a1} = ef - H + h_c \\ h_{a2} = 0.5 \times \left(k + \sqrt{k^2 + 4 \times (10.31 h_b + h_b h_c + 11.32 ef - h_c ef)}\right) \\ k = -10.31 + h_b + h_c + ef \\ n = \dfrac{s_b^2}{2g} \\ f = 1 + \lambda \dfrac{c}{j} + \eta \end{cases} \qquad \text{Equation 1-2}$$

In the equations, $h_a$—water level elevation at the water inlet in meters, $h_{a1}$, $h_{a2}$—respective calculated intermediate quantities of ha in meters, k—calculated intermediate quantity, e—calculated intermediate quantity, f—calculated intermediate quantity, H—maximum water lifting height in meters that the natural atmospheric pressure at the measurement site can provide, which maximum water lifting height is an empirical value or a measurement record, $h_c$—maximum elevation at the top of the aqueduct in meters, which maximum elevation is an experimental parameter/measurement data, $h_p$—water level elevation at the drainage outlet in meters, which water level elevation is a measurement record, $s_b$—flow rate at the drainage outlet of the aqueduct in m/s, which flow rate is a measurement record, g—gravitational acceleration in m/s², which is a constant, λ—resistance coefficient of the aqueduct along the path, which resistance coefficient is determined according to the prior art, C—length of the aqueduct in meters, which length is an experimental parameter, j—inner diameter of the aqueduct in meters, which inner diameter is an experimental parameter, and η—local resistance/head loss coefficient of the aqueduct, which local resistance/head loss coefficient is determined according to the prior art.

The above groundwater level elevation measurement method is based on the principle of connectors and is implemented by means of a technical solution of leading groundwater above the ground for measurement. Due to the complexity of the "buried" environment of groundwater, using the principle of connectors to measure the water level of underground sites on the ground requires considering the impact of the siphon head on the surface outflow rate. A large number of experimental studies in the early stage of the present invention found that in a measurement system built using the principle of connectors, the liquid flow rate in an aqueduct is not determined by the liquid level difference between two ports of the aqueduct, but is affected by both the difference value between H and the siphon head Ho of the aqueduct, as well as the elevation difference value between a water inlet and a drainage outlet of the aqueduct. On the basis of establishing an analysis model of this impact, the present invention provides the above technical solution that is different from the existing "burial depth" type measurement.

The above groundwater level elevation measurement method is suitable for situations where the pressure at the water inlet of the aqueduct is significantly higher than the pressure at the drainage outlet. Under certain working conditions, the water outflow cannot be stabilized automatically after the equipment is installed, so that the optimization of the above measurement method is to introduce a negative pressure device. Specifically, the drainage outlet of the aqueduct is connected to the negative pressure device, and the negative pressure device is used to create a pressure difference between two ports of the aqueduct; water outflow is induced from the drainage outlet, and the pressure is stabilized; and when the water outflow from the drainage outlet is stable, the water level elevation ha at the water inlet is calculated according to Equation 2, $$h_a = h_b + \frac{y_b}{\mu g} + ef \quad \text{Equation 2}$$

In the equation, $y_b$—stabilized voltage value (kpa) of the negative pressure device, which stabilized voltage value is a measurement record; and u-groundwater density (kg/m³), which is a measurement record or a constant.

The present invention also relates to an optimized design using devices in the measurement method, including the following aspects.

The permeable cylinder is of a coaxial multi-layer telescopic casing structure. A wall of each layer of a casing is covered with permeable holes, and the permeable holes are as fine as possible to reduce water inflow disturbance. A conical permeable stone is provided at the end of a core casing of the permeable cylinder. An outer wall of each layer of the casing and the outer perimeter of the conical permeable stone are both wrapped with a highly permeable fabric. The inner diameter of the aqueduct is not greater than 4 mm.

In order to ensure the measurement effect, when drilling to install the permeable cylinder, the permeable stone extends into 3.5 m to 6.5 m below the groundwater level, and as large an elevation difference as possible between the water inlet and the drainage outlet of the aqueduct is ensured when the equipment is installed.

The groundwater level elevation measurement method of the present invention only requires unobstructed constructed pipelines to implement measurement. After the pipelines are filled and the water outflow is stable, there is no specific requirement for the water outflow for each measurement. Once the flow rate is detected, the water outflow can be turned off. Therefore, in the case of using a high-precision micro-liquid flow meter, an extremely fine aqueduct can be used, the detection of sp is only completed instantaneously, and the disturbance to the groundwater level elevation is extremely small and can be ignored.

Based on the above groundwater level elevation measurement method, the present invention also provides a groundwater storage monitoring and measurement system, with the technical solution as follows.

A groundwater storage monitoring and measurement system, where a groundwater measurement space is defined; measurement sites $A_i$ in the measurement space are determined and designed by using the permeability, hydraulic gradient and terrain slope of the watershed rock and soil in a monitoring area, all $A_i$ constituting a three-dimensional measurement point array $A_{3D}$; groundwater level elevation data $h_{ai}$ of all $A_i$ at different times t is measured and collected by using the above groundwater level elevation measurement method to obtain a data set D) of the point array $A_{3D}$, the set D containing each $h_{ai}$ in the point array $A_{3D}$ and $A_i$ numbers corresponding thereto, spatial coordinates, and time; and water storage characteristic data of the groundwater measurement space is constructed by using the set D.

In the above groundwater storage monitoring and measurement system, depending on the data in the set D, the water storage characteristic data of the groundwater measurement space can be dynamic and/or static data/graphs/models/equations, etc.

The present invention also provides an application solution of the above groundwater storage monitoring and measurement system.

The application of above groundwater storage monitoring and measurement system is characterized in that the groundwater storage monitoring and measurement system is applied to groundwater monitoring and early warning. The groundwater storage monitoring and measurement system is used to monitor changes in groundwater characteristics, and issue warning information according to preset conditions.

In the above application solution, groundwater monitoring and early warning can also include a water quality testing device, which simultaneously realizes the functions of testing the quality of groundwater and issuing warning information according to preset conditions.

Compared with the prior art, the beneficial effects of the present invention are: (1) The groundwater level measurement method of the present invention is a new concept that is different from the existing "burial depth" type "in-situ measurement" technical framework. On the basis of solving the key technical problems of the difference value between the maximum water lifting height that needs to be calculated and that the natural atmospheric pressure at the measurement site can provide and the siphon lift of the aqueduct, as well as the joint impact of the elevation difference value between the water inlet and the drainage outlet of the aqueduct on the liquid flow rate in the aqueduct in the problem of using the principle of connectors to measure the groundwater level elevation through drainage flow rate above the ground, the present invention provides a brand-new technical solution for groundwater level measurement. (2) Since the outlet flow rate is used as a monitoring indicator, this technical solution can introduce the existing mature technology of flow rate detection into measurement systems to improve the measurement accuracy at a low technical cost. Compared with existing measurement technology, which is a technology improvement pathway that improves sensitivity to liquid level changes in underground sites at the expense of equipment sophistication or the creation of a closed underground measurement environment, this technical solution has obvious advantages. (3) This technology can reduce the equipment accuracy of underground working parts to a certain extent, thereby relaxing installation and construction conditions; and meanwhile, this technology also enhances the controllability of measurement operations on the ground. Therefore, the technology as a whole has better adaptability. (4) This technology can effectively prevent cost losses caused by maintenance damage to underground working parts.

Respective numerical marks in the accompanying drawings are:
1 permeable cylinder, 11 casing, 12 permeable hole, 13 core casing, 14 permeable stone, 2 aqueduct, 21 water inlet, 22 drainage outlet, 3 negative pressure device, 4 flow rate measuring instrument, 5 groundwater level, and 6 soil body/soil layer.

DETAILED DESCRIPTION

The preferred embodiments of the present invention will be further described below with reference to the accompanying drawings.

Embodiment 1

As shown in FIGS. 1 to 5, the method of the present invention is used to design a groundwater monitoring system solution for a small watershed, for measuring a groundwater elevation and estimating a water storage.

1. Watershed On-Site Investigation and Instrument Layout

The studied small watershed (hereinafter referred to as the monitoring area) is located in Fenghua City, Zhejiang Province. The entire watershed is trumpet-shaped, with a watershed area of 0.17 km² and rich groundwater resources.

Figure 1:
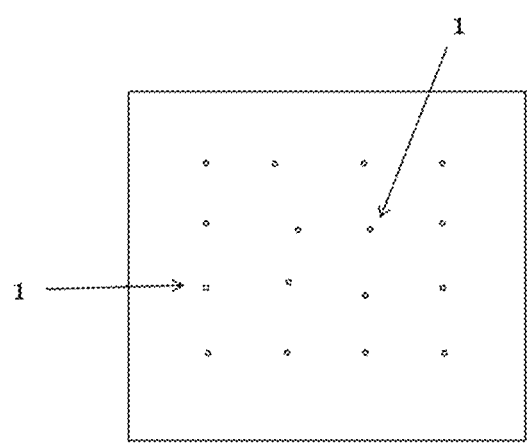
FIG. 1 is a schematic top view of the groundwater level monitoring sites in the monitoring area.

On-site surveys acquire basic data, including the permeability, hydraulic gradient, terrain slope, etc. of the rock and soil in the monitoring area. According to the basic data, sites with relatively flat terrain in a small area that is convenient for drilling construction are selected as the measurement sites, and a drilling installation and layout method is adopted. According to the on-site drilling construction conditions and hydrogeological conditions, since the monitoring area is relatively small and the geological structure is relatively single, the drilling interval is set to 20 m, and drilling sites are added in corresponding areas with large terrain changes (as shown in FIG. 1). Each drilling site $A_i$ is marked with a corresponding coordinate $A(x, y, z)$. All $A_i$ constitute a three-dimensional measurement point array $A_{3D}$.

Figure 2:
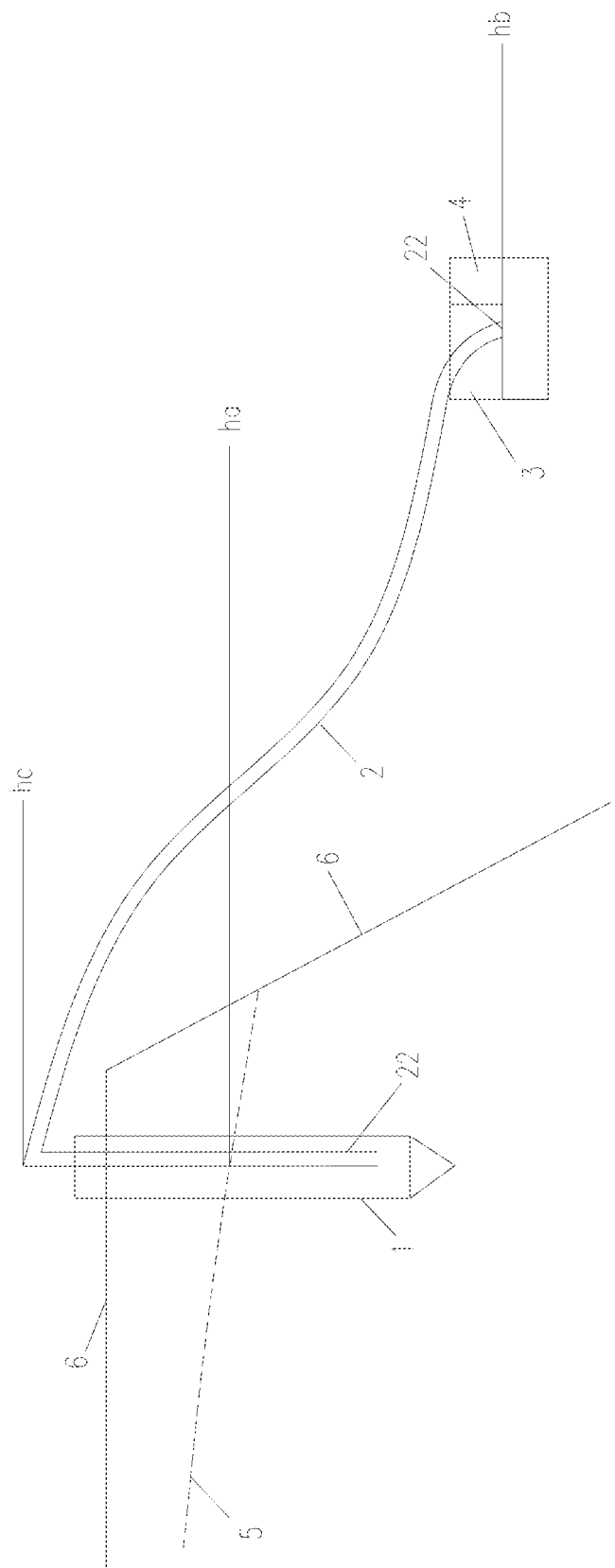
FIG. 2 is a schematic structural diagram of the groundwater storage monitoring and measurement system.
Figure 3:
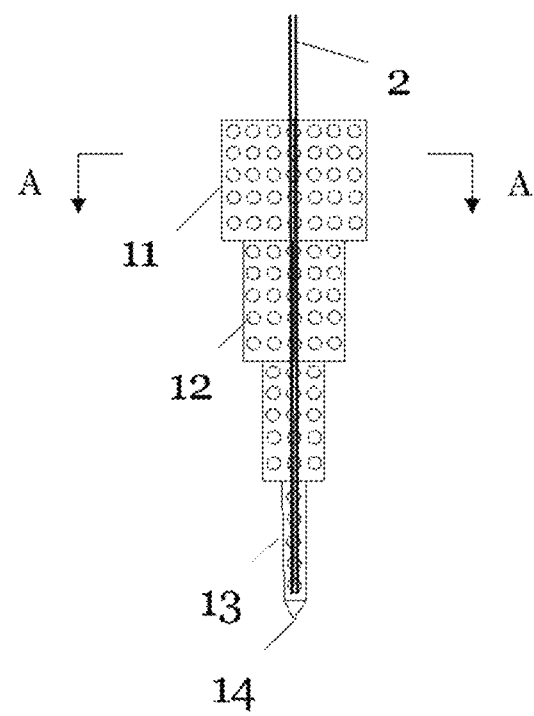
FIG. 3 is a schematic diagram of the external structure of the permeable cylinder (showing the extended state of each layer of casing).
Figure 4:
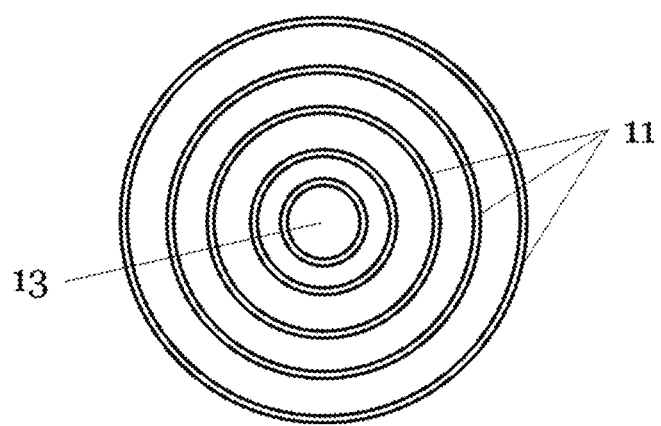
FIG. 4 is a schematic structural diagram of the A-A section in FIG. 3.

FIG. 2 is a schematic structural diagram of the groundwater storage monitoring and measurement system; FIG. 3 is a schematic structural diagram of the permeable cylinder; and FIG. 4 is a schematic structural diagram of the A-A section in FIG. 3.

The permeable cylinder (1) is of a coaxial telescopic casing structure, a wall of each layer of a casing (11) is covered with permeable holes (12), a conical permeable stone (14) is provided at the end of a core casing (13), and an outer wall of the casing (11) and the outer perimeter of the conical permeable stone (14) are wrapped with a highly permeable fabric. In this embodiment, geotextile is chosen as the highly permeable fabric.

The permeable tube (1) is placed in the borehole to ensure that the permeable stone (14) extends 3.5 m to 6.5 m below the groundwater level. When the groundwater soaks into the core casing (13), the aqueduct (2) extends into the permeable tube (1), and the water inlet (21) is submerged under the liquid level in the core casing (13). The drainage outlet (22) of the aqueduct (2) is pulled above the ground to connect the flow rate measuring instrument (4). It is ensured there is an elevation difference between the water inlet (21) and the drainage outlet (22) of the aqueduct (2), and the elevation of the drainage outlet (22) is as low as possible below that of the water inlet (21). In this embodiment, a high-precision micro-liquid flow meter is selected as the flow rate measuring instrument (4).

Whether the drainage outlet (22) at each monitoring site can naturally and stably discharge water is tested. Monitoring sites that can stably discharge water are classified as Class A sites, and the rest are classified as Class B sites.

2. Measurement of Groundwater Level Elevations at Monitoring Sites

A groundwater level elevation at each monitoring site is measured, where Class A sites are applicable to a measurement plan A, and Class B sites are applicable to a measurement plan B. The following takes one monitoring site each of the two classes of sites A and B as an example to describe the measurement processes of the measurement plans A and B. Unless otherwise specified, the measurement methods for similar sites are the same.

2.1 Measurement Plan A

For monitoring sites of a sample A, various types of data are collected. The resistance coefficient $\lambda$ of the aqueduct along the path is calculated and determined based on the prior art (determined by experience), the local resistance coefficient n of the aqueduct is determined by actual measurement, and the flow rate at the drainage outlet Sp is measured under a stable water outflow state of the drainage outlet. Respective parameters are substituted into the equation set of Equation 1 for calculation (g=9.8 m/s²). Relevant data are shown in Table 1.

2.2 Measurement Plan B

For monitoring sites of a sample B, the drainage outlet (22) of the aqueduct (2) is connected to the negative pressure device (3). The negative pressure device (3) is adjusted to create a pressure difference between two ports of the aqueduct (2), inducing water to flow out of the drainage outlet (22) and stabilizing the negative pressure. When the water outflow from the drainage outlet (22) is stable, the reading $y_b$ of the negative pressure device (3) and the water outflow rate sp at the drainage outlet (22) are recorded. The remaining data collection methods are the same as in Section 2.1.

Respective parameters are substituted into Equation 2 for calculation (g=9.8 m/s²). Relevant data are shown in Table 1.

TABLE 1

Related data of groundwater elevation measurement at monitoring sites of sample A and sample B

| | | monitoring sites of sample A | monitoring sites of sample B |
|---|---|---|---|
| experimental parameters | length C of aqueduct | 20 m | 15 m |
| | inner diameter j of aqueduct | 4 × 10⁻³ m | |
| | maximum water lifting height H that local natural atmospheric pressure can provide | 11.32 m | |
| | resistance coefficient λ of aqueduct along the path | 0.0371 | 0.0580 |
| | groundwater density μ | / | |
| measurement data | local resistance coefficient η of aqueduct | 1.5 | 1.0 |
| | maximum elevation $h_c$ at the top of aqueduct | 500.321 m | 510.365 m |
| | water level elevation $h_b$ at drainage outlet | 487.676 m | 507.462 m |
| | stabilized voltage $y_b$ of negative pressure | / | −40 kpa |
| | flow rate $s_b$ at drainage outlet | 0.586 m/s | 0.375 m/s |
| calculated intermediate quantity | k | 1001.579 | / |
| | e | 0.0175 m | 0.00717 |
| | f | 188 | 219.5 |
| | $h_{a1}$ | 492.291 m | / |
| | $h_{a2}$ | 1206.670 m | / |
| Measurement result | water level elevation $h_a$ at water inlet | 492.291 m | 505.006 m |

3. Drawing of a Three-Dimensional Map of Groundwater Level Elevations in the Watershed Groundwater level elevation data $h_{ai}$ of all $A_i$ in the point array $A_{3D}$ is collected to obtain a groundwater data set D of the point array $A_{3D}$. The set D contains the groundwater elevation value $h_{ai}$ of each monitoring site $A_i$, and numbers, spatial coordinates, measurement time t and other data of each $A_i$, describing the groundwater characteristics of the monitoring area.

Figure 5:
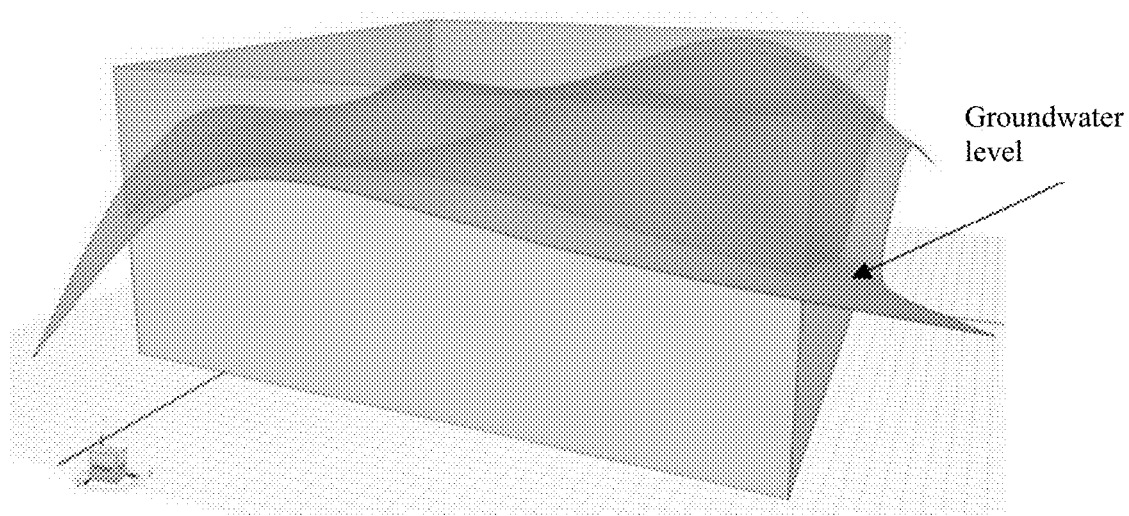
FIG. 5 is a schematic diagram of the three-dimensional groundwater level elevation in the groundwater measurement space in the monitoring area (the arrow in the figure indicates the groundwater level).

The set D is used to construct water storage characteristic data of the groundwater measurement space. Specifically, the groundwater level elevation data $h_{ai}$ of each monitoring site $A_i$ is interpolated to obtain a three-dimensional groundwater level elevation map of the groundwater measurement space in the monitoring area. FIG. 5 is a schematic diagram of the three-dimensional groundwater level elevation in the groundwater measurement space in the monitoring area, and the arrow in the figure indicates the groundwater level. By collecting $h_{ai}$ values of each $A_i$ at different times, a groundwater dynamic model in the groundwater measurement space in the monitoring area can be established. Based on the three-dimensional model, the groundwater storage in the groundwater measurement space in the monitoring area can be calculated.

4. Expansion of an Early Warning Function of the Groundwater Storage Monitoring and Measurement System In the groundwater storage monitoring and measurement system, a monitoring threshold condition is added to an upper computer, and various real-time monitoring data or preliminary calculation values are compared with a threshold, enabling a preliminary assessment of groundwater changes and the issuance of an early warning signal when necessary according to preset conditions. By adding a water quality testing unit, the safety of the quality of groundwater can also be tested, and an early warning signal can be issued when necessary as well according to preset conditions.

What is claimed is:

1. A groundwater level elevation measurement method, wherein a hole is drilled at a measurement site and a permeable cylinder (1) is placed to ensure that groundwater enters the permeable cylinder (1), a water inlet (21) of an aqueduct (2) extends below the liquid level in the permeable cylinder (1), and a drainage outlet (22) of the aqueduct (2) is led to the ground; and after the drainage outlet (22) discharges water steadily, a water level elevation $h_a$ at the water inlet (21) is calculated according to an equation set of Equation 1, $$h_a = \min(h_{a1}, h_{a2}) \quad \text{Equation 1-1}$$

$$\begin{cases} h_{a1} = ef - H + h_c \\ h_{a2} = 0.5 \times \left(k + \sqrt{k^2 + 4 \times (10.31 h_b + h_b h_c + 11.32 ef - h_c ef)}\right) \\ k = -10.31 + h_b + h_c + ef \\ n = \dfrac{s_b^2}{2g} \\ f = 1 + \lambda \dfrac{c}{j} + \eta \end{cases} \quad \text{Equation 1-2}$$

in the equations, $h_a$—water level elevation at the water inlet (21) in meters, $h_{a1}$, $h_{a2}$—respective calculated intermediate quantities of $h_a$ in meters, k—calculated intermediate quantity, e—calculated intermediate quantity, f—calculated intermediate quantity, H—maximum water lifting height in meters that the natural atmospheric pressure at the measurement site can provide, which maximum water lifting height is an empirical value or a measurement record, $h_c$—maximum elevation at the top of the aqueduct (2) in meters, which maximum elevation is an experimental parameter/measurement data, $h_b$—water level elevation at the drainage outlet (22) in meters, which water level elevation is a measurement record, $s_b$—flow rate at the drainage outlet (22) of the aqueduct (2) in m/s, which flow rate is a measurement record, g—gravitational acceleration in m/s², which is a constant, λ—resistance coefficient of the aqueduct (2) along the path, which resistance coefficient is determined according to the prior art, C—length of the aqueduct (2) in meters, which length is an experimental parameter, j—inner diameter of the aqueduct (2) in meters, which inner diameter is an experimental parameter, and η—local resistance/head loss coefficient of the aqueduct (2), which local resistance/head loss coefficient is determined according to the prior art.

2. The water level elevation measurement method according to claim 1, wherein the drainage outlet (22) of the aqueduct (2) is connected to a negative pressure device (3), and the negative pressure device (3) is used to create a pressure difference between two ports of the aqueduct (2); water outflow is induced from the drainage outlet (22), and the pressure is stabilized; and when the water outflow from the drainage outlet (22) is stable, the reading $y_b$ of the negative pressure device (3) is recorded, the water outflow rate $s_b$ at the drainage outlet (22) is recorded, and the water level elevation $h_a$ at the water inlet (21) is calculated according to Equation 2, $$h_a = h_b + \frac{y_b}{\mu g} + ef \qquad \text{Equation 2}$$

in the equation, $y_b$—stabilized voltage value of the negative pressure device (3) in kpa, which stabilized voltage value is a measurement record, and μ—groundwater density in kg/m³, which is a measurement record or a constant.

3. The water level elevation measurement method according to claim 1, wherein a micro liquid flow meter is used to detect sp, and once sp is recorded, the drainage outlet (22) is immediately closed.

4. The water level elevation measurement method according to claim 3, wherein the permeable cylinder (1) is of a coaxial multi-layer telescopic casing structure, a wall of each layer of a casing (11) is covered with permeable holes (12), a conical permeable stone (14) is provided at the end of a core casing (13), and an outer wall of the casing (11) and the outer perimeter of the conical permeable stone (14) are wrapped with a highly permeable fabric.

5. The water level elevation measurement method according to claim 4, wherein the inner diameter j of the aqueduct (2) is less than or equal to 4 mm, and the aperture of the permeable holes (12) is not greater than 5 mm.

6. The water level elevation measurement method according to claim 5, wherein when drilling to install the permeable cylinder (1), the permeable stone (14) extends into 3.5 m to 6.5 m below the groundwater level, and an elevation difference between the water inlet (21) and the drainage outlet (22) of the aqueduct (2) is ensured when the equipment is installed.

7. A groundwater storage monitoring and measurement system, wherein a groundwater measurement space is defined; measurement sites $A_i$ in the measurement space are determined and designed by using the permeability, hydraulic gradient and terrain slope of the rock and soil in a monitoring area, all $A_i$ constituting a three-dimensional measurement point array $A_{3D}$; groundwater level elevation data $h_{ai}$ of all $A_i$ at different times t is measured and collected by using the groundwater level elevation measurement method described in claim 6 to obtain a data set D of the point array $A_{3D}$, the set D containing each $h_{ai}$ in the point array $A_{3D}$ and $A_i$ numbers corresponding thereto, spatial coordinates, and time; and water storage characteristic data of the groundwater measurement space is constructed by using the set D.

8. The groundwater storage monitoring and measurement system according to claim 7, wherein the water storage characteristic data of the groundwater measurement space includes dynamic and/or static data/graphs/models/equations.

9. An application of the groundwater storage monitoring and measurement system according to claim 7, wherein the system is applied to groundwater monitoring and early warning; and the groundwater storage monitoring and measuring system is used to monitor changes in groundwater characteristics, and issue warning information according to preset conditions.

10. The application according to claim 9, further comprising a water quality testing device, which is used to test the quality of groundwater and issue warning information according to preset conditions.

\* \* \* \* \*